(12) United States Patent
Yu (10) Patent No.: US 10,725,535 B2
(45) Date of Patent: *Jul. 28, 2020

(54) HEAD-WORN IMAGE DISPLAY APPARATUS FOR STEREOSCOPIC MICROSURGERY

(71) Applicant: Steven Sounyoung Yu, Fairfax, VA (US)

(72) Inventor: Steven Sounyoung Yu, Fairfax, VA (US)

(*) Notice: Subject to any disclaimer, the term of this patent is extended or adjusted under 35 U.S.C. 154(b) by 12 days.

This patent is subject to a terminal disclaimer.

(21) Appl. No.: 16/283,804

(22) Filed: Feb. 24, 2019

(65) Prior Publication Data

US 2019/0201161 A1    Jul. 4, 2019

Related U.S. Application Data

(63) Continuation of application No. 15/208,600, filed on Jul. 12, 2016, now Pat. No. 10,222,619.

(Continued)

(51) Int. Cl.
*G06F 3/01* (2006.01)
*G02B 21/00* (2006.01)

(Continued)

(52) U.S. Cl.
CPC ............. *G06F 3/011* (2013.01); *A61B 90/30* (2016.02); *A61B 90/361* (2016.02); *A61B 90/37* (2016.02); *A61B 90/50* (2016.02); *G02B 21/0012* (2013.01); *G02B 27/0172* (2013.01); *H04N 13/239* (2018.05); *H04N 13/344* (2018.05); *A61B 2034/107* (2016.02); *A61B 2090/3616* (2016.02); *A61B 2090/371* (2016.02); *A61B 2090/372* (2016.02); *A61B 2090/502* (2016.02);

(Continued)

(58) Field of Classification Search
CPC ............. H04N 13/0239; H04N 13/044; H04N 13/239; H04N 13/344; A61B 90/50; A61B 90/37; A61B 90/361; A61B 90/30; A61B 2034/107; A61B 2090/371; A61B 2090/502; A61B 2090/372; G02B 27/0172; G02B 2027/0178; G02B 2027/0138; G02B 2027/0134; G02B 21/0012; G06F 3/011; G06F 3/012; G06F 3/013

See application file for complete search history.

(56) References Cited

U.S. PATENT DOCUMENTS 5,526,184 A * 6/1996 Tokuhashi ........... G02B 27/017
                                                          359/489.07
6,133,944 A * 10/2000 Braun .................... H04N 5/232
                                                              348/39

(Continued)

*Primary Examiner* — Darlene M Ritchie (57) ABSTRACT

A head-worn image display apparatus that comprises a non-immersive image display assembly that receives images from a stereoscopic video camera module. The image display assembly comprises a miniature display component for generating the images for display. The image display assembly may work by an optical relay system. The head-worn image display apparatus could be used in a variety of different settings. One particular application is for performing medical procedures such as microsurgery. The stereoscopic video camera module may have optical magnification capability (e.g. such as in a surgical microscope) to provide a magnified view of the surgical field.

20 Claims, 10 Drawing Sheets

Related U.S. Application Data (60) Provisional application No. 62/191,461, filed on Jul. 12, 2015.

(51) Int. Cl.

| | | |
|---|---|---|
| *A61B 90/30* | (2016.01) | |
| *H04N 13/239* | (2018.01) | |
| *H04N 13/344* | (2018.01) | |
| *A61B 90/00* | (2016.01) | |
| *G02B 27/01* | (2006.01) | |
| *A61B 90/50* | (2016.01) | |
| *H04N 13/204* | (2018.01) | |
| *A61B 34/10* | (2016.01) | |

(52) U.S. Cl.
CPC ............ *G02B 2027/0134* (2013.01); *G02B 2027/0138* (2013.01); *G02B 2027/0178* (2013.01); *H04N 13/204* (2018.05)

(56) References Cited

U.S. PATENT DOCUMENTS

| | | | | | |
|---|---|---|---|---|---|
| 6,353,503 | B1* | 3/2002 | Spitzer | ................ | G02B 27/017 359/630 |
| 6,356,392 | B1* | 3/2002 | Spitzer | ................ | G02B 27/017 345/8 |
| 7,824,052 | B1* | 11/2010 | Halm | ................ | A61B 90/35 362/105 |
| 7,891,808 | B2* | 2/2011 | Mazurenko | ................ | G02B 7/002 351/158 |
| 8,941,559 | B2* | 1/2015 | Bar-Zeev | ................ | G02B 26/026 345/7 |
| 9,870,060 | B2* | 1/2018 | Marggraff | ................ | G06F 3/017 |
| 2005/0277913 | A1* | 12/2005 | McCary | ................ | G02B 21/0012 606/1 |
| 2007/0075917 | A1* | 4/2007 | Nishi | ................ | A63F 13/08 345/8 |
| 2007/0083098 | A1* | 4/2007 | Stern | ................ | A61B 1/0016 600/407 |
| 2010/0026787 | A1* | 2/2010 | Yasuda | ................ | H04N 13/344 348/47 |
| 2010/0240988 | A1* | 9/2010 | Varga | ................ | G02B 27/017 600/425 |
| 2011/0145978 | A1* | 6/2011 | Harbin | ................ | A61B 90/35 2/209.13 |
| 2014/0066701 | A1* | 3/2014 | Wilson | ................ | A61B 1/00009 600/102 |
| 2015/0138248 | A1* | 5/2015 | Schrader | ................ | G02B 27/017 345/690 |
| 2015/0173846 | A1* | 6/2015 | Schneider | ................ | A61B 1/00009 600/424 |
| 2015/0260992 | A1* | 9/2015 | Luttmann | ................ | G02B 27/0172 359/631 |
| 2016/0209648 | A1* | 7/2016 | Haddick | ................ | G02B 27/0093 |
| 2016/0220105 | A1* | 8/2016 | Duret | ................ | A61B 6/022 |
| 2016/0220324 | A1* | 8/2016 | Tesar | ................ | G02B 21/0012 |
| 2016/0262608 | A1* | 9/2016 | Krueger | ................ | A61B 3/0041 |
| 2016/0291688 | A1* | 10/2016 | Hirota | ................ | G06F 3/14 |
| 2017/0042631 | A1* | 2/2017 | Doo | ................ | A61B 90/37 |
| 2017/0083084 | A1* | 3/2017 | Tatsuta | ................ | G06F 3/147 |
| 2017/0318235 | A1* | 11/2017 | Schneider | ................ | G02B 27/2228 |
| 2017/0325907 | A1* | 11/2017 | Maeda | ................ | G06F 3/01 |

\* cited by examiner

FIG. 3 image center

Left Side · Right Side

HEAD-WORN IMAGE DISPLAY APPARATUS FOR STEREOSCOPIC MICROSURGERY

TECHNICAL FIELD

My invention relates to head-worn displays, also known as head-mounted displays, for viewing images.

BACKGROUND

In surgical procedures, in order to get a close-up or magnified view of an operative site on a patient, there are two options available to the surgeon. One option is to wear surgical loupes, which are special glasses that have magnification lenses mounted thereon. However, there are numerous ergonomic problems with surgical loupes. The lenses add significant weight to the glasses, causing it to push down against the surgeon's nose and cheeks, and also causing the glasses to slide down the bridge of the nose. Moreover, because of the fixed angle of the lenses, the surgeon must often hunch over the operative site.

Another option is to use a surgical microscope, which is positioned over the surgical field. By viewing through the microscope eyepieces, the surgeon has a close-up or magnified view of the surgical field. However, this has its own ergonomic problems as well. The surgeon must maintain an awkward posture to peer through the eyepiece, which can cause back and neck fatigue. Also, constantly viewing through a binocular microscope can cause eyestrain. In summary, these prior art techniques for performing microsurgery can be very uncomfortable to the surgeon, causing them to suffer from neck strain, back strain, and eye fatigue.

SUMMARY

In one embodiment, my invention is a head-worn image display apparatus comprising: (a) a support frame; (b) a non-immersive image display assembly that is in communication with and receives video images from a stereoscopic video camera module that captures left and right-side images, the display assembly comprising: (i) a first display component that generates the left-side images for display; (ii) a second display component that generates the right-side images for display; (iii) a left-side optical image surface or interface to provide the left-side image for viewing by the user's left eye, wherein the image surface or interface is at least partially transparent; (iv) a right-side optical image surface or interface to provide the right-side image for viewing by the user's right eye, wherein the image surface or interface is at least partially transparent; (v) wherein the distance between the center of the left-side image surface or interface, and the center of the right-side image surface or interface is 10 cm or less.

In some embodiments, the displayed image does not change based on tracking of the user's head position or movement. In some embodiments, each of the left-side image and the right-side image occupies less than 40° horizontally in the user's visual field. In some embodiments, the display assembly further comprises one or more light occlusion elements that can change the amount of light transmitted through each image surface or interface.

In some embodiments, the first display component is located on the left side and comprises a display panel, and the left-side image surface or interface is the display panel of the first display component; and the second display component is located on the right side and comprises a display panel, and the right-side image surface or interface is the display panel of the second display component. In some cases, the distance between the center of the left display panel and the center of the right display panel is 10 cm or less.

In some embodiments, the display assembly comprises an optical relay system in which the left-side image surface or interface is a left-side projection surface with the image from the first display component being relayed to the projection surface for viewing by the user's left eye; and in which the right-side image surface or interface is a right-side projection surface with the image from the second display component being relayed to the projection surface for viewing by the user's right eye. In some cases, the distance between the center of the left-side projection surface and the center of the right-side projection surface is 10 cm or less.

In another embodiment, my invention is a head-worn image display apparatus comprising: (a) a support frame; (b) a non-immersive image display assembly that is in communication with and receives video images from a stereoscopic video camera module that captures left and right-side images, the display assembly comprising: (i) a first display component that generates the left-side images for display; (ii) a second display component that generates the right-side images for display; (iii) a left-side optical image surface or interface to provide the left-side image for viewing by the user's left eye, wherein the image surface or interface is at least partially transparent; (iv) a right-side optical image surface or interface to provide the right-side image for viewing by the user's right eye, wherein the image surface or interface is at least partially transparent; (v) one or more light occlusion elements that can change the amount of light transmitted through each image surface or interface.

In some embodiments, the one or more light occlusion elements can be user-controlled to adjust the amount of light transmitted through each image surface or interface. In some embodiments, the displayed image does not change based on tracking of the user's head position or movement. In some embodiments, each of the left-side image and the right-side image occupies less than 40' horizontally in the user's visual field.

In some embodiments, the first display component is located on the left side and comprises a display panel, and the left-side image surface or interface is the display panel of the first display component; and the second display component is located on the right side and comprises a display panel, and the right-side image surface or interface is the display panel of the second display component. In some cases, the distance between the center of the left display panel and the center of the right display panel is 10 cm or less.

In some embodiments, the display assembly comprises an optical relay system in which the left-side image surface or interface is a left-side projection surface with the image from the first display component being relayed to the projection surface for viewing by the user's left eye; and in which the right-side image surface or interface is a right-side projection surface with the image from the second display component being relayed to the projection surface for viewing by the user's right eye. In some cases, the distance between the center of the left-side projection surface and the center of the right-side projection surface is 10 cm or less.

In another embodiment, my invention is a stereoscopic video system comprising: a head-worn image display apparatus; and a controller (e.g. foot-operated controller) for controlling the head-worn display apparatus. In some embodiments, the system further comprises a stereoscopic video camera module. In some embodiments, the controller also controls the stereoscopic video camera module.

In another embodiment, my invention is a stereoscopic video system comprising: a head-worn image display apparatus; and a stereoscopic video camera module that is in communication with the head-worn display apparatus. In some embodiments, the system further comprises a controller for controlling the stereoscopic video camera module. In some embodiments, the controller controls the head-worn image display apparatus. In some embodiments, the controller controls both the head-worn image display apparatus and the stereoscopic video camera module.

In another embodiment, my invention is a method of performing a medical procedure, comprising: (a) directing a stereoscopic video camera module to the site of the medical procedure to capture left and right-side images; (b) wearing a head-worn image display apparatus that comprises: (i) a support frame; (ii) a non-immersive image display assembly that is in communication with and receives video images from the stereoscopic video camera module, the display assembly comprising: a first display component that generates the left-side images for display; a second display component that generates the right-side images for display; a left-side optical image surface or interface to provide the left-side image for viewing by the user's left eye, wherein the image surface or interface is at least partially transparent; a right-side optical image surface or interface to provide the right-side image for viewing by the user's right eye, wherein the image surface or interface is at least partially transparent; and (c) performing the medical procedure while viewing the video images provided by the head-worn display apparatus.

In some embodiments, the center of each image is located in a lower or medial half of each of the user eye's visual field. In some embodiments, the method further comprises controlling the amount of light transmitted through each image surface or interface. In some embodiments, the stereoscopic camera module has optical magnification capability, and the images provided are magnified views of the medical procedure site. In some embodiments, the method further comprises adjusting the amount of magnification in the view of the medical procedure site. In some embodiments, the image display assembly simultaneously provides both a magnified view of the medical procedure site as well as a direct view of the medical procedure site.

The steps of this method may be performed in any suitable order. For example, the step of wearing the head-worn image display could be performed before the step of directing the stereoscopic video camera module, or alternatively, in reverse order. In another example, the surgeon may repeat the step of directing the stereoscopic video camera module to make adjustments while performing the medical procedure.

DETAILED DESCRIPTION

My invention relates to a binocular head-worn image display apparatus which provides computer-processed images for the user's view. The head-worn apparatus is coupled to a stereoscopic camera module (physically or wirelessly) to receive the images produced by the stereoscopic camera module and displays them as real-time video for the user's view. The head-worn apparatus comprises a support frame that is configured to be worn on the user's head. Examples of suitable configurations for the support frame include eyewear, glasses, goggles, headband, helmet, face shield, head gear, face mask, visor, headset, etc. The head-worn apparatus can be designed to fit over or around the user's own eyeglasses or mounted on the user's eyeglasses. As will be described in more detail below, FIGS. 1A and 1B and FIGS. 2A-2C show examples of head-worn image display apparatuses of my invention. The head-worn apparatus uses an optical "see through" video image display system in which the computer-processed image is superimposed as an overlay onto a direct, real-world view of the environment. The head-worn apparatus may use any suitable optical "see-through" video image display technology.

The head-worn apparatus further comprises a non-immersive image display assembly mounted on the support frame. The display assembly is in communication, directly or indirectly, with a stereoscopic camera module. The display assembly may receive the image data via a physical connection (e.g. a wire) or a wireless connection via a wireless receiver. The display assembly receives the image data from the stereoscopic camera module and produces display images from the image data. The display assembly may include any of various conventional components for carrying out this function, including display controllers, microprocessors, image processors, video processors, or other circuitry for handling image signals.

The display assembly comprises a miniature display component which produces the images for display to the user. The miniature display component may use any suitable display technology that can be miniaturized to the dimensions suitable for use in a head-worn display apparatus. Examples of display technologies include active-matrix liquid-crystal displays (AM-LCDs), light-emitting diodes (LED), organic light-emitting diodes (OLED), laser diode, ferroelectric liquid-crystal-on-silicon (LCOS), time-multiplex optical shutter (TMOS), etc. The image display assembly comprises a first miniature display component that generates the left-side stereoscopic image; and a second miniature display component that generates the right-side stereoscopic image.

The image display assembly comprises a left-side optical see-through image surface or interface to provide the left-side overlay image for viewing by the user's left eye. The display assembly further comprises a right-side optical see-through image surface or interface to provide the right-side overlay image for viewing by the user's right eye. Each of the right-side and left-side image surfaces or interfaces is at least partially transparent to allow "see through" viewing. In my invention, the head-worn display apparatus does not change the displayed overlay image based on tracking of the user's head position or movement (e.g. it may lack the gyroscopes or accelerometers that allow this type of tracking). This absence of tracking is particularly advantageous if the head-worn apparatus is being used for performing a medical procedure. In this context, the user may wish to keep focus on the medical procedure site and does not want the view shifting with head movement.

In some embodiments, the distance between the center of the left-side overlay image and the center of the right-side overlay image is 10 cm or less; in some cases, 9 cm or less; in some cases, 8 cm or less; in some cases, 7 cm or less. The distance between the left and right-side images may be adjustable to accommodate for user size, preference, or measurements.

Figure 3:
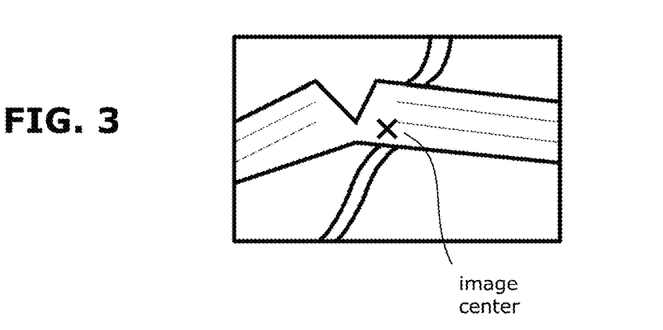
FIG. 3 shows the center of an image indicated by the "x" mark.
Figure 4:
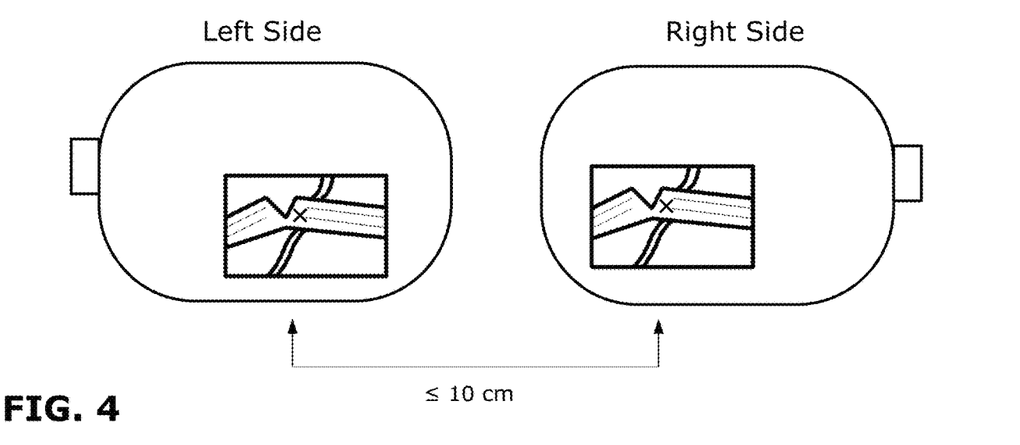
FIG. 4 shows an example configuration in which the distance between the center of the left-side image and the center of the right-side image is 10 cm or less.

For regularly-shaped images such as squares, rectangles, circles, or ovals, conventional geometric calculations can be used to find the image center (e.g. the intersection of the central vertical and central horizontal axes). For example, FIG. 3 shows the center of the left-side image being displayed in the apparatus of FIG. 2 (discussed in more detail below). The image itself is a magnified view of an operative site that exposes a damaged nerve and a small blood vessel traversing across it. Careful microscopic surgery is required to repair this damaged nerve while avoiding injury to the blood vessel. The center of the image is indicated by the "x" mark, which is the location where the central horizontal axis and the central vertical axis of the rectangular-shape image intersect. In the example shown in FIG. 4, the distance between the center of the left-side image and the center of the right-side image is 10 cm or less.

For images having other shapes or configurations, the center of the image can be calculated in any suitable way. For example, for irregularly-shaped images, the first moments of the image shape (which gives the center of mass) may be used as the image center. For example, for an irregularly-shaped image that is defined by the function b(x,y)=[1 for image points, 0 for non-image points], the first moments of the object are:

$$\bar{x} = \frac{\int\int x \cdot b(x, y) dx dy}{\int\int b(x, y) dx dy}$$

$$\bar{y} = \frac{\int\int y \cdot b(x, y) dx dy}{\int\int b(x, y) dx dy}$$

In some embodiments, the distance between the center of the left-side image interface or surface and the center of the right-side image surface or interface is 10 cm or less; in some cases, 9 cm or less; in some cases, 8 cm or less; in some cases, 7 cm or less. The center of the image interface or surface can be determined in the same or similar manner as described above for the center of the image. The size of the "see-through" image surface or interface (left and right) is sufficiently small to be mounted on a head-worn apparatus. The image interface or surface may be 4 cm or less as measured along its widest dimension (e.g. for a rectangular shape, along its diagonal dimension).

The computer-processed image generated by the miniature display component can be presented to the user's eye via a direct optical path or an indirect optical path. The overlay image may be presented directly by a configuration in which the miniature display component is placed in front of the user's eye (i.e. the user is directly viewing the image on the miniature display component). In some embodiments, the left-side image surface or interface is the display panel of the miniature display component located on the left side for displaying the left-side computer-processed overlay image; and the right-side image surface or interface is the display panel of the miniature display component located on the right side for displaying the right-side computer-processed overlay image. In some cases, the distance between the center of the left display panel and the center of the right display panel is 10 cm or less; in some cases, 9 cm or less; in some cases, 8 cm or less; in some cases, 7 cm or less. The center of the display panel can be determined in the same or similar manner as described above for the center of the image. So that it can be mounted on a head-worn apparatus, the dimensions for the display panel may be 4 cm or less as measured along its widest dimension (e.g. for a rectangular shape, along its diagonal dimension).

Figure 1A:
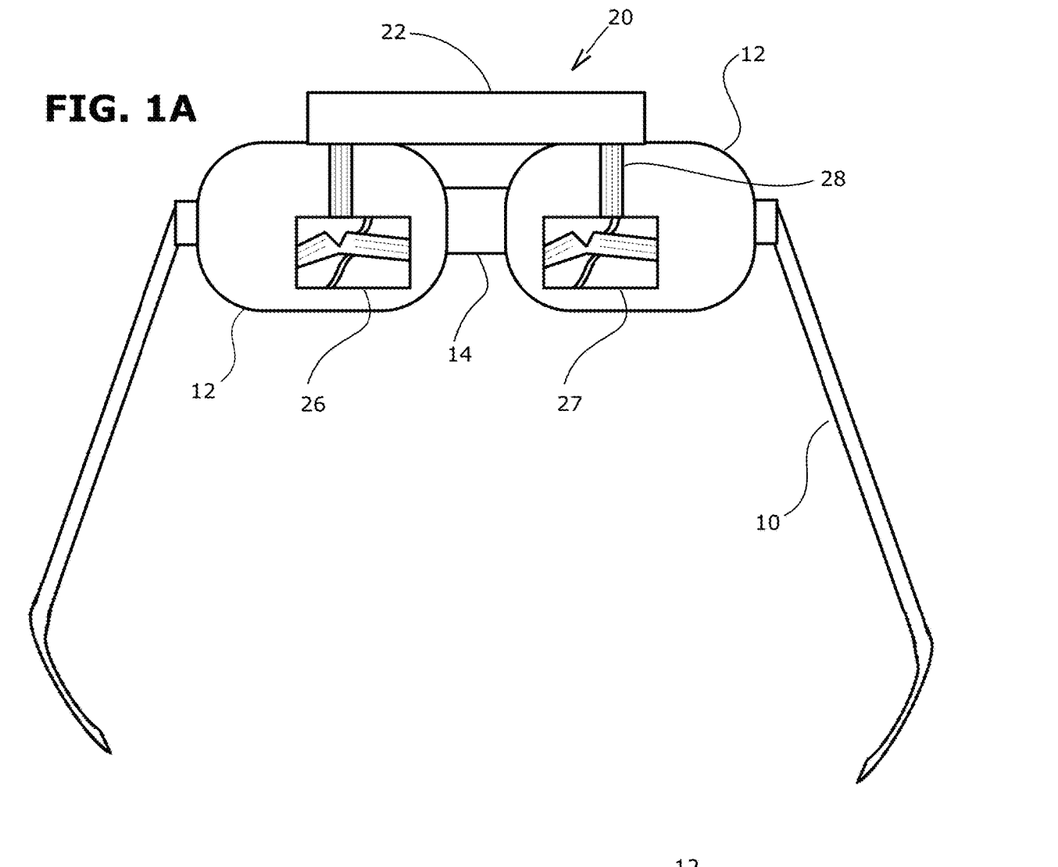
FIGS. 1A and 1B show an example of a head-worn image display apparatus of my invention.
Figure 1B:
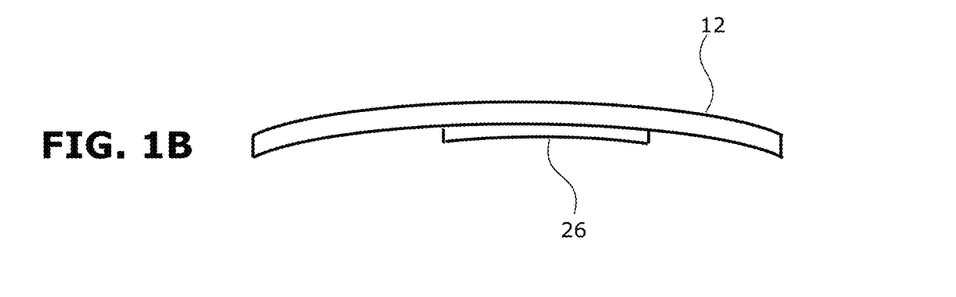

FIGS. 1A and 1B show an example of a head-worn image display apparatus of my invention. The support frame 10 is configured as a safety eyeglass with transparent eye shields 12 connected by a nose bridge 14 and sidearms to secure it to the user's nose or face. FIG. 1A shows a back/inside view of the apparatus (from the point-of-view of the user); FIG. 1B shows a top view of the left transparent eye shield 12. Mounted on the support frame 10 is an image display assembly 20 which comprises a radio receiver device that is connected to a miniature computer 22 for on-board computing. The image display assembly 20 also comprises two curved transparent OLED (organic light-emitting diode) display devices, one for the left side and one for the right side. Each OLED device comprises a display panel such that there is a right-side display panel 27 and a left-side display panel 26. The miniature computer 22 contains a display controller that controls and drives the OLED display devices via a transparent ribbon interconnect 28.

Any of a variety of different types of configurations may be suitable for presenting the overlay image to the user's eye via an indirect optical path. In some embodiments, the image display assembly comprises an optical relay system in which the computer-processed overlay image is projected onto a projection surface that is placed in front of the user's eye (i.e. the projection surface is the image surface or interface). The optical relay system transmits or relays the overlay image from the miniature display component located remotely from the projection surface to the user's eye. There is a left-side projection surface that optically receives the computer-processed image displayed by the first display component and redirects it to the user's left eye; and a right-side projection surface that optically receives the computer-processed image displayed by the second display component and redirects it to the user's right eye.

In some embodiments, the distance between the center of the left-side projection surface and the center of the right-side projection surface is 10 cm or less; in some cases, 9 cm or less; in some cases, 8 cm or less; in some cases, 7 cm or less. The center of the projection surface can be determined in the same or similar manner as described above for the center of the image. The size of the "see-through" projection surface (left and right) is sufficiently small to be mounted on a head-worn apparatus. The projection surface may be 4 cm or less as measured along its widest dimension (e.g. for a rectangular shape, along its diagonal dimension).

The optical relay system can use any of a variety of different types of optical elements that work by refraction, diffraction, reflection, or otherwise, including diffraction gratings, reflective mirrors (e.g. half-silvered mirrors), prisms, waveguides (also known as light-guides or light-pipes), lenses, holographic optical elements, Fresnel lens, phase conjugate materials, reflective or refractive interfaces (such as an interface of two transparent materials of different refractive indices), etc. The head-worn apparatus may use any suitable optical relay system or optical design to provide images with a "see-through" capability. Various types of designs for optical relay systems that can be used in my invention are described by Ozan Cakmakci & Jannick Rolland, "Head-Worn Displays: A Review," in *Journal of Display Technology*, vol. 2:3 (Sep. 2006). The optical relay system may use any optical "see-through" video image display technology, including those using curved mirror and waveguide technologies. Examples of waveguide technologies that can be used include diffractive waveguides (slanted diffraction nanometer gratings) developed by Nokia and used in Vuzix's STAR 1200XLD; holographic waveguides used by Sony and Konica Minolta; polarized waveguides used by Lumus; reflective waveguides used by Epson in their Moverio BT-100 and BT-200 products and Google in their Google Glass product; the "Clear-Vu" reflective waveguide (thin monolithic molded plastic with surface reflectors and conventional coatings) used by Optinvent in their ORA-1 and ORA-2 smart glasses; the DigiLens waveguide lenses developed by SBG Labs; tapered opaque light guides used by Olympus; or virtual retinal displays (also known as a retinal scan display or retinal projector) that draws a raster display directly onto the retina of the eye. Other products using optical relay systems include the R-7 Glasses by Osterhout Design Group, the Meta 2 glasses by the Meta Company, and the SmartEyeglass by Sony Corp. Other examples of head-worn display designs or optical designs that can be used in my invention are described in patent publications US 2014/0211289 (Makiko Hino et al., Seiko Epson); US 2013/0076599 (Hitoshi Saito, Seiko Epson); US 2011/0043436 (Masao Yamamoto, Scalar Corp.); U.S. Pat. No. 8,384,999 (David Crosby et al., Cerr Ltd.); US 2010/0202048 (Yaakov Amitai et al.); US 2011/0213664 (Ralph F. Osterhout et al.); U.S. Pat. No. 6,356,392 (Mark Spitzer, Microoptical Corp.); U.S. Pat. No. 9,310,559 (John Macnamara; Magic Leap, Inc.).

The computer-processed overlay image may be blended to any degree with the real-world external scene. The overlay image may appear as a semi-transparent or translucent "ghost-like" object in front of the external scene. However, the "bleed-through" of the external scene may make viewing of the overlay image difficult. For example, in the context of a microsurgery procedure, viewing of small or fine anatomic structures may be obscured by the "bleed-through" of the background scene.

In some embodiments, the image display assembly has adjustable transparency for the optical "see-through" image surface or interface. This can allow the display assembly to be changed from a "see-through" image display system to a "see-around" display system in which the overlay image occludes the view of the external scene. In some embodiments, the display assembly further comprises a light occlusion element that can prevent light from the external scene being transmitted through the image surface or interface and reaching the user's eyes. By reducing or blocking out the transmission of light coming in from the external scene and mixing into the overlay image, visualization of the overlay image can be enhanced (e.g. brighter colors, better contrast, better definition, etc.).

Any of a variety of different types of techniques for light occlusion may be used in my invention, including those that use thin films (such as liquid crystal films, electrochromic films, photochromic films, or similar type of coatings), polarizing filters, reversible electrochemical mirrors, transition-metal switchable glass or mirrors, digital micromirror devices, adjustable partial reflectors, spatial light modulators, or mechanical shutters or covers. These may be controllable (e.g. electrochemically or electromechanically) to turn the transparency on/off or adjust the amount of transparency.

In some embodiments, the opacity of the light occlusion element is controlled (e.g. electrically) by the user. The user may be able to switch the light occlusion element from being transparent to opaque, or vice versa. In this way, the user can switch the display assembly back and forth between operating in a "see-through" mode (overlay image is transparent) and operating in a "see-around" mode (overlay image is opaque). Alternatively, the user may be able to control the opacity of the light occlusion element within a continuum between transparency and opaqueness.

The light occlusion element may be located in any suitable position. For example, the light occlusion element may be positioned as a transmission mask as in U.S. Pat. No. 6,037,914 (Ian Robinson, Hewlett-Packard Co.), or as a spatial light modulator as in U.S. Pat. No. 7,639,208 (Ha et al., Univ. of Central Florida), or as an opacity filter as in U.S. Pat. No. 8,941,559 (Avi Bar-Zeev et al., Microsoft Corp.), or over or on lenses of the display assembly. The light occlusion element may be a standalone element or an integral part of another component of the display assembly. Examples of light occlusion elements and how they are used for light occlusion are described in patent publications U.S. Pat. No. 5,526,184 (Yuki Tokuhashi et al., Olympus Optical); U.S. Pat. No. 6,037,914 (Ian Robinson, Hewlett-Packard Co.); U.S. Pat. No. 7,639,208 (Ha et al., Univ. of Central Florida); U.S. Pat. No. 8,941,559 (Avi Bar-Zeev et al., Microsoft Corp.); US 2001/0000677 (Akinari Takagi et al.); US 2014/0177023 (Chunyu Gao et al., Augmented Vision Inc.).

Figure 2A:
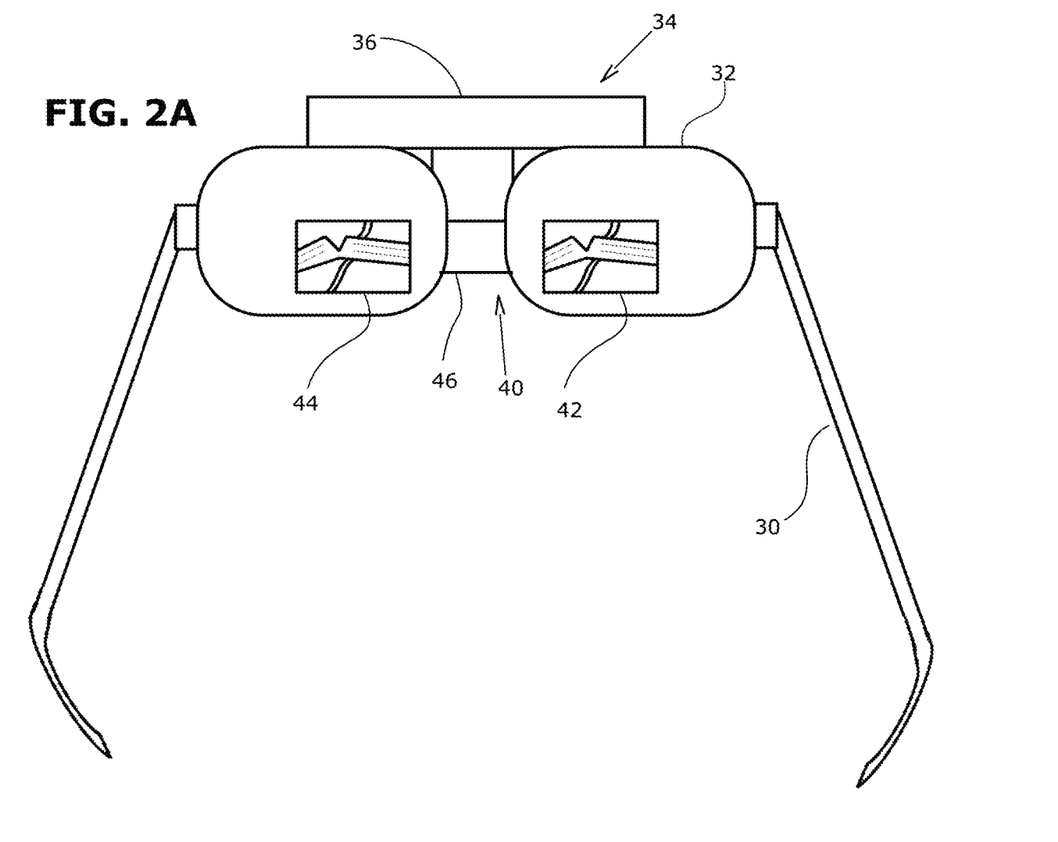
FIGS. 2A-2C show another example of a head-worn image display apparatus of my invention.
Figure 2B:
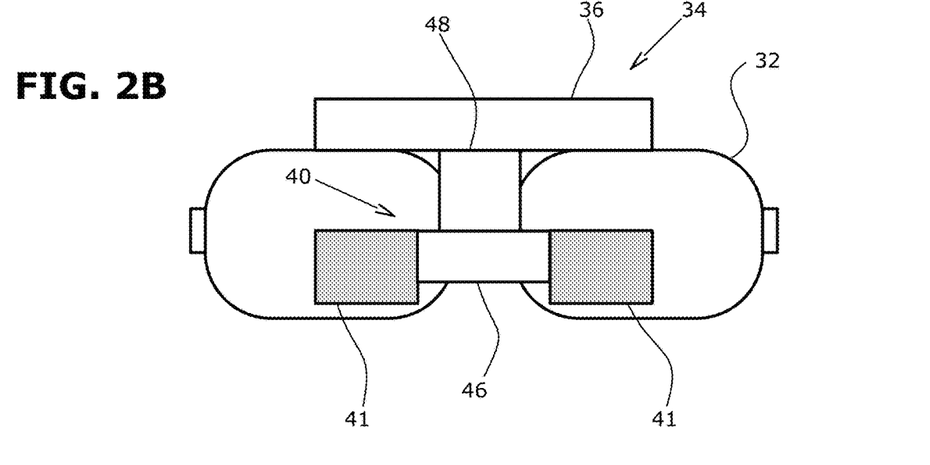
Figure 2C:
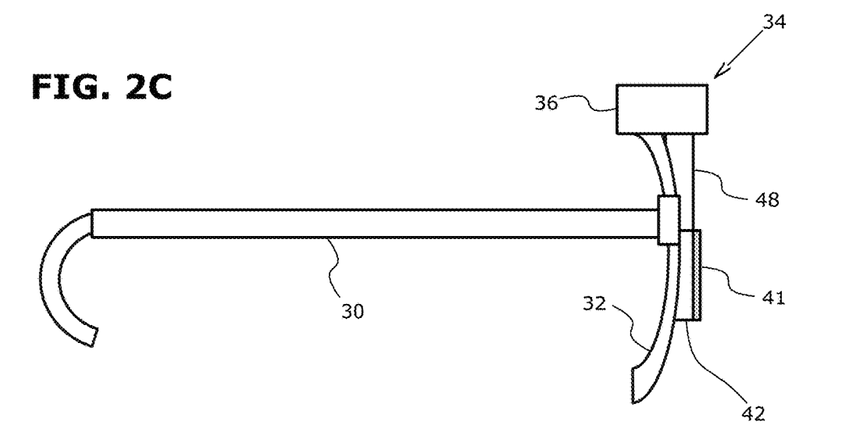

FIGS. 2A-2C show another example of a head-worn image display apparatus of my invention. FIG. 2A shows a back/inside view of the apparatus (from the point-of-view of the user); FIG. 2B shows an front/outside view of the apparatus; FIG. 2C shows a right-side view. The head-mounting support frame 30 for the apparatus is a safety glass frame with transparent eye shields 32. Mounted on the support frame 30 is an image display assembly 34 which comprises a radio receiver device that is connected to a miniature computer 36 for on-board computing. The image display assembly 34 also comprises an optical relay system 40. The optical relay system 40 comprises a right projection surface 42 (for displaying the right-side image), a left projection surface 44 (for displaying the left-side image), and a light-guide substrate 46 which serves as a conduction medium for relaying the images to the projection surfaces.

A nose bridge 48 for the frame 30 serves as a conduit for the conductive wiring from a display controller in the miniature computer 36 that drives the LCOS display (not shown) contained within the optical imaging system. As shown in FIGS. 2B and 2C, positioned in front of each of the projection surfaces 42 and 44 are liquid crystal screens 41 that can be controlled to adjust the transparency of the projection surfaces 42 and 44 to the external scene.

Figure 5:
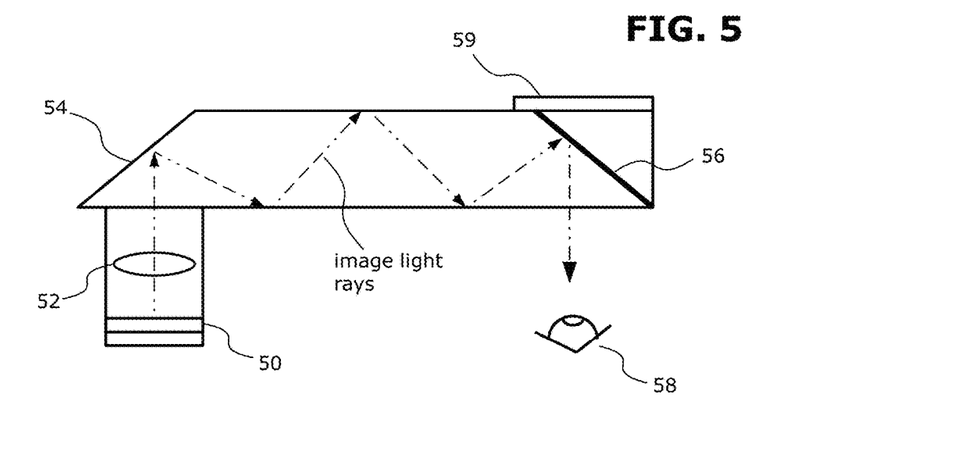
FIG. 5 shows one example of an image display assembly for projecting the computer-processed overlay image to the user's eye.

FIG. 5 (top view) shows one example of an image display assembly for projecting the computer-processed overlay image to the user's eye. The image is generated on a display panel 50 (i.e. the miniature display component). One or more projection lenses 52 magnify the displayed image. The light rays of the image enter a transparent plastic substrate 54 (light-guide). By total internal reflection within the substrate 54, the light rays of the image are projected onto a half-mirror layer 56 (i.e. the projection surface). This half-mirror layer directs the image-forming light rays out (outcouples) of the substrate 54 so that the image gets delivered to the user's eye 58.

The display assembly further comprises an adjustable liquid crystal transparency screen 59 on the external surface of the substrate 54 (facing externally) limited to the area encompassed by the overlay image being projected (here the area of the half-mirror 56). The transparency screen 59 can be switched back-and-forth from a transparent mode to an opaque mode by the user. When the transparency screen 59 is in the transparent mode, light incoming from the external scene is mixed with the overlay image through the half-mirror 56, or the overlay image may be turned off so that an unobstructed transparent view of the external environment is provided. When the transparency screen 59 is in the opaque mode (the liquid crystal elements become opaque), the light incoming from the external scene is blocked. This blocks the portion of the external view that would otherwise be seen through ("bleed-through") the overlay image.

Figure 6A:
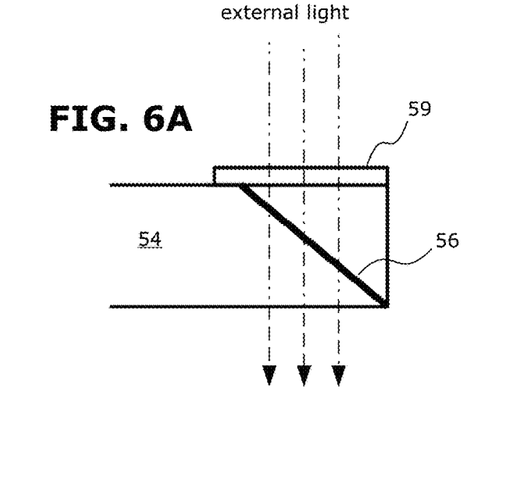
FIGS. 6A and 6B show the operation of the liquid crystal transparency screen in FIG. 5.
Figure 6B:
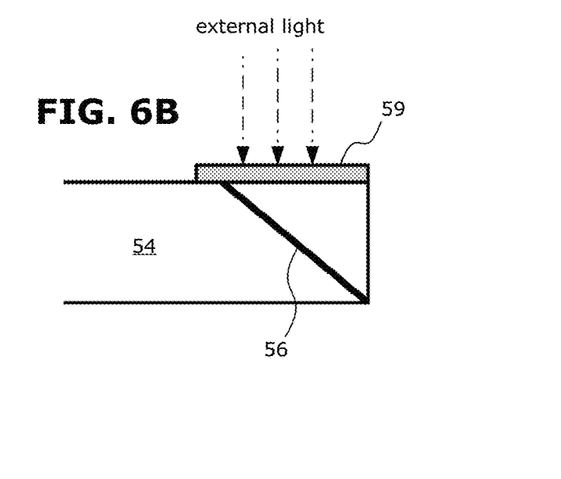

FIGS. 6A and 6B (top views) show the operation of the liquid crystal transparency screen. In FIG. 6A, the liquid crystal film 59 is set to full transparency mode such that the incoming light from the external scene is mixed with the projected overlay image through the half-mirror 56. Some of the "real world" external scene may be visible as background in the projected overlay image. In FIG. 6B, the user switches the liquid crystal transparency screen 59 to opaque mode (i.e. block the transmission of light). This blocking of the external scene enhances viewing of the projected overlay image.

Figure 7A:
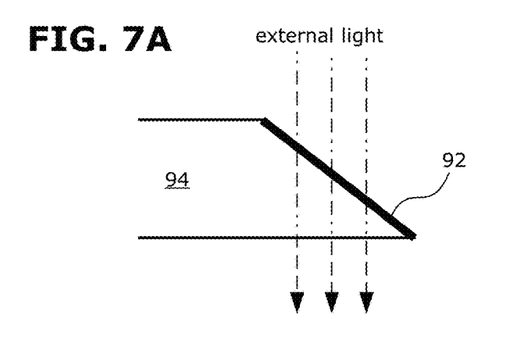
FIGS. 7A and 7B show another example of how a light occlusion element can work.
Figure 7B:
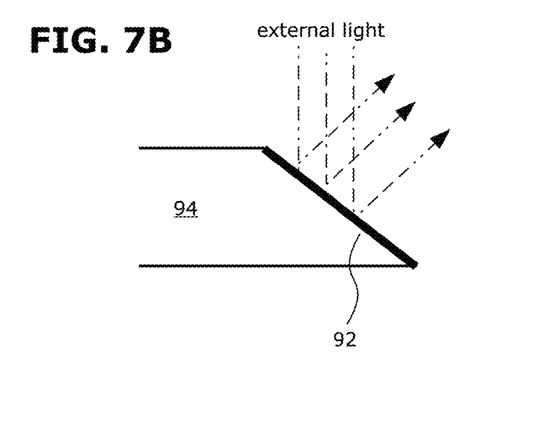

FIGS. 7A and 7B (top views) show another example of how a light occlusion element can work. Here, a half-mirror 92 is located at the end of a light-guide substrate 94. The half-mirror 92 itself can be made to be variably transparent/opaque under user control. In FIG. 7A, the half-mirror 92 is set to full transparency such that the incoming light from the external scene is mixed with the projected overlay image through the half-mirror 92. Some of the "real world" external scene may be visible as background in the projected overlay image. In FIG. 7B, the half-mirror 92 is set to fully reflect the incoming light from the external scene, thereby blocking the transmission of light through the half-mirror 92. This blocks the portion of the external view that would otherwise be seen through the overlay image. This blocking of the external scene enhances viewing of the projected overlay image.

Figure 8A:
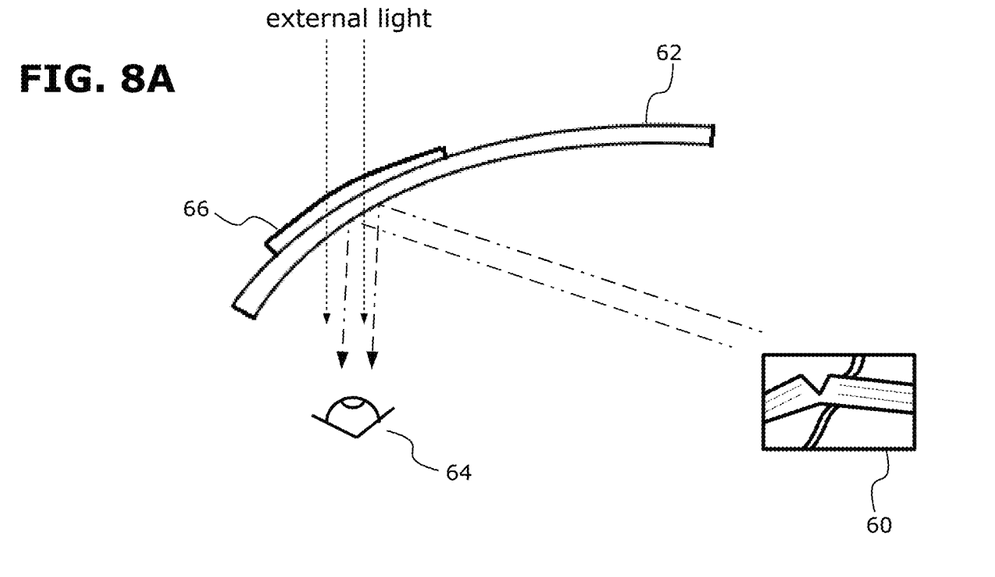
FIGS. 8A and 8B show another example of an optical design for projecting the image to the user's eye.
Figure 8B:
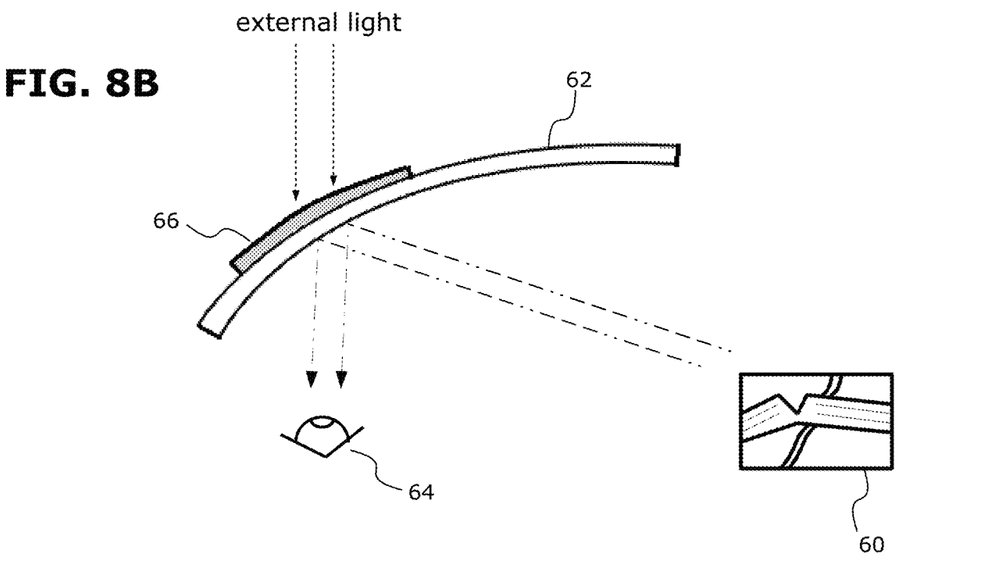

FIGS. 8A and 8B (top views) show another example of an optical design for projecting the image to the user's eye. An image 60 is produced on a miniatures display component and projected towards a curved half-silvered mirror 62, which then reflects the projected image to the user's eye 64. The curved mirror 62 is coated with an adjustable liquid crystal film 66 on the external surface of the curved mirror 62 (facing externally) limited to the area encompassed by the overlay image being projected. The liquid crystal film 66 can be changed from transparent to opaque (and vice versa). In FIG. 8A, the liquid crystal film 66 is set to full transparency such that the incoming light from the external scene is mixed with the projected overlay image. Some of the "real world" external scene may be visible as background in the projected overlay image. In FIG. 8B, the user switches the liquid crystal film 66 to opaque mode (i.e. block the transmission of light). This blocks the portion of the external view that would otherwise be seen through the projected overlay image, thereby enhancing viewing of the projected overlay image.

In some embodiments, the head-worn display apparatus further comprises an illumination source to illuminate the scene being viewed (e.g. medical procedure site). The illumination source may be any conventional lighting component that produces visible light of sufficient intensity for illumination, such as LED, xenon, halogen, incandescent, etc.

Figure 9:
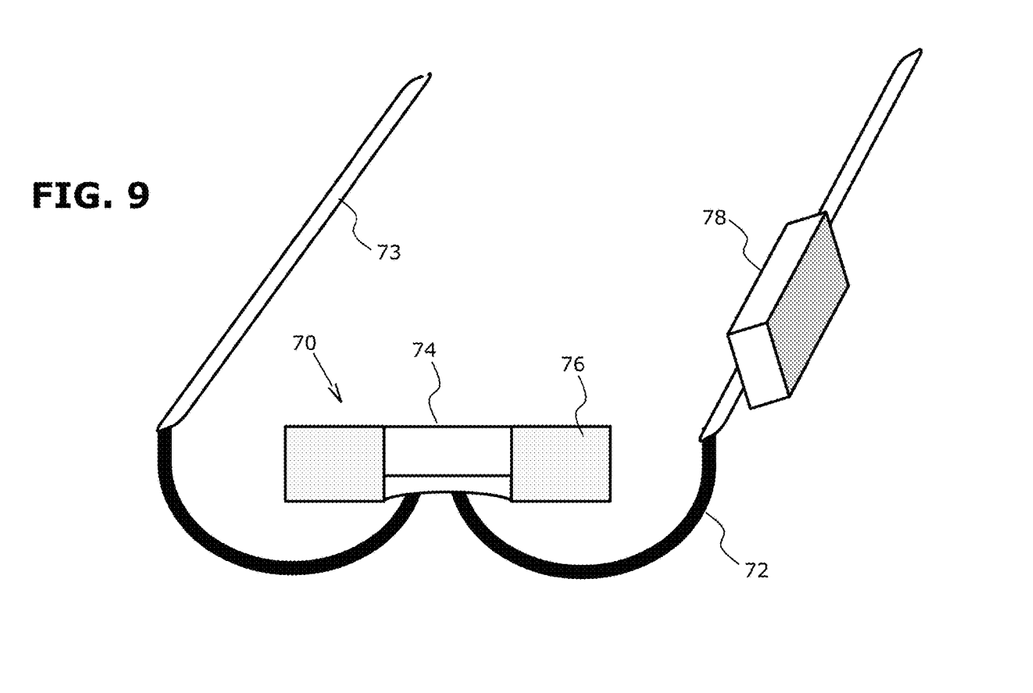
FIG. 9 shows another example of a head-worn display apparatus of my invention.
Figure 10:
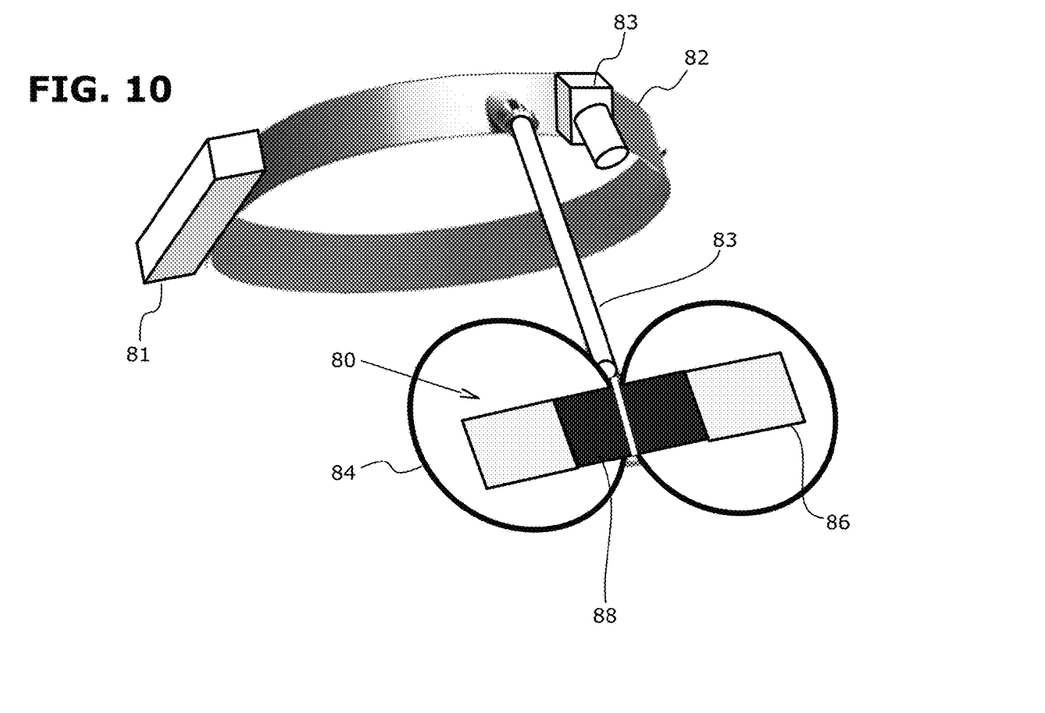
FIG. 10 shows another example of a head-worn display apparatus of my invention.

FIG. 9 shows an example of a head-worn display apparatus in which the image display assembly 70 is mounted on an eyeglass frame 72 that lacks a transparent eye shield. The display assembly 70 comprises a light-guide substrate 74 and two projection panels 76. The display assembly 70 is in communication with a microcomputer 78 mounted on the sidearms 73 of the eyeglass frame 72. FIG. 10 shows an example of a head-worn display apparatus in which the display assembly 80 is suspended in front of the user's eyes from a head band 82 by a support fixture 83 holding two transparent eye shields 84. The display assembly 80 is in communication with a microcomputer 81 mounted on the head band 82. The apparatus could be designed such that the display assembly 80 can be swung or swiveled out of the user's line-of-sight. Also mounted on the head band 82 is an illumination light 83 for illuminating the scene being viewed. The display assembly 80 comprises two transparent OLED display panels 86 and two mechanically-operated shutters 88 that slide over in front of the OLED display panels 86 when activated to block out the incoming light from the external scene.

The head-worn apparatus may be part of a stereoscopic video system. In some embodiments, the stereoscopic video system comprises a controller, which may control the head-worn apparatus (such as the image display assembly) or another component of the stereoscopic video system. The control signals may be transmitted by a physical (e.g. wired) or wireless connection. The controller may control one or more operations of the head-worn apparatus. In some embodiments, the controller controls the display of the overlay image (e.g. switching the overlay image on and off). If the head-worn apparatus comprises a light occlusion element, in some embodiments thereof, the controller controls the light occlusion element (e.g. switching the light occlusion element between transparency and opaque mode, or adjusting the degree of transparency); in some cases, the controller controls both the display of the overlay image and the light occlusion element (e.g. cycling from activating display of the overlay image with the light occlusion element in transparent mode, to switching the light occlusion element to opaque mode, and then to deactivating display of the overlay image with returning of the light occlusion element to the transparent mode).

In some embodiments, the controller controls a stereoscopic camera module, as will be described below. Various operations of the stereoscopic camera module may be controlled by the controller, including adjusting magnification, focus, and position such as angle, distance from the target, etc. The controller may be operated by the user or by someone else (e.g. in an operating room setting, by an operating room technician). This controller may use any suitable type of user interface (e.g. touchscreen, touch panel, buttons, switches, keyboard, mouse, trackball, dial wheels, voice activation, hand gesture recognition, etc.). In some embodiments, the controller operates in a hands-free or touch-free manner (e.g. voice activation, hand gesture recognition, foot-operated, etc.). In some embodiments, the controller is a foot-operated controller (i.e. operated by the user's foot, such as a foot pedal). A foot-operated controller can allow for hands-free operation.

In some embodiments, the stereoscopic video system comprises a stereoscopic video camera module. The head-worn display apparatus is physically separate from the stereoscopic video camera module and receives, directly or indirectly, real-time video images from the stereoscopic video camera module. The video camera module may be a single integrated unit or in separate components (e.g. lens and digital image sensor on one part, connected to image and video processing components located remotely from the lens and image sensor). An example of a stereoscopic camera module that can be used in my invention is shown in patent publication WO 01/05161 (Guy Kuskas, Surgivision), which is incorporated by reference herein.

Figure 11:
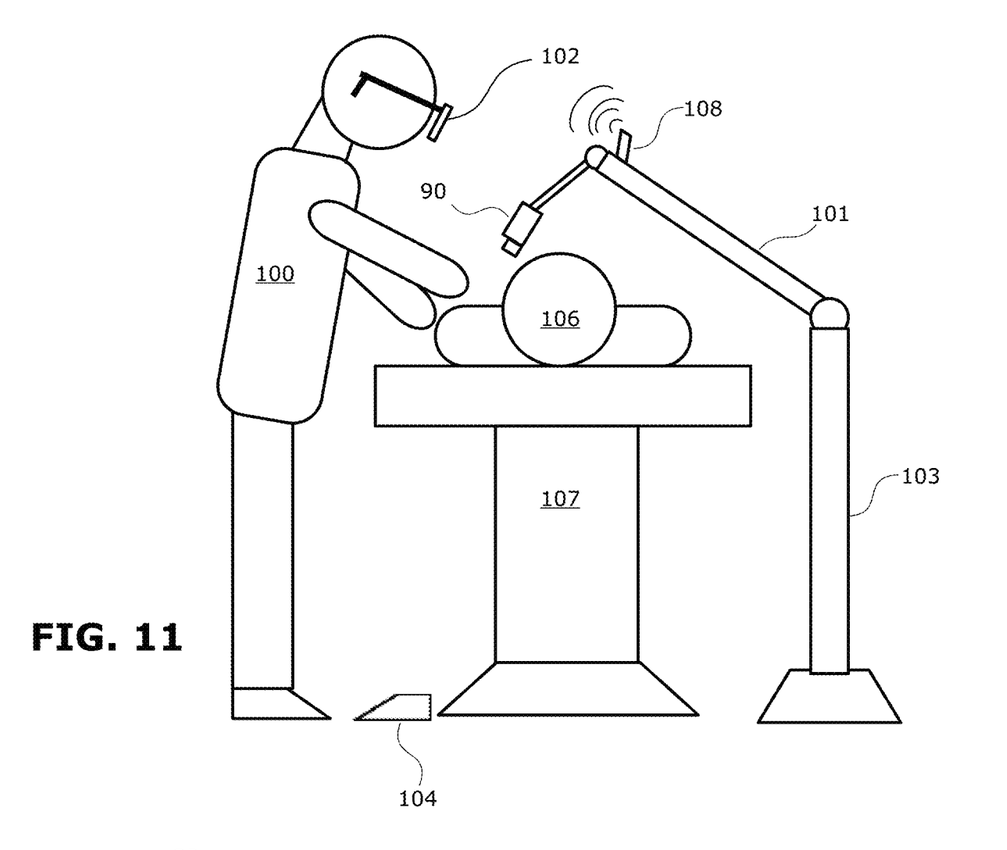
FIG. 11 shows an example of a medical procedure being performed using a stereoscopic video system.
Figure 12A:
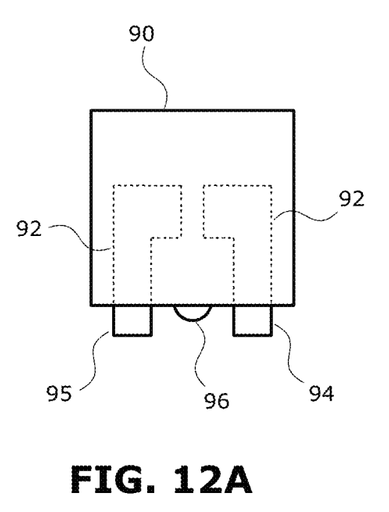
FIGS. 12A and 12B show more detailed drawings of the example camera module shown in FIG. 11.
Figure 12B:
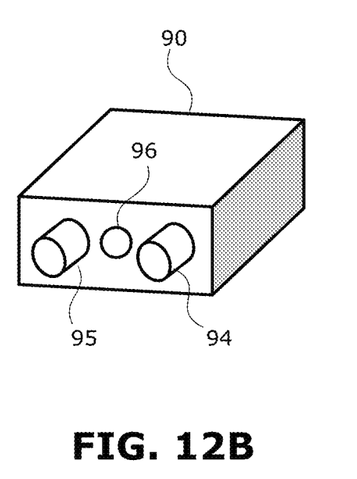

FIGS. 12A (top view) and 12B (perspective view) show more detailed drawings of an example camera module 90 in the stereoscopic video system shown in FIG. 11, to be described in more detail below. Inside the camera module 90 is a conventional digital camera device 92 for acquiring digital images, one for the left lens assembly 94 and the other for the right lens assembly 95, to produce a pair of stereoscopic images. The two cameras 92 are mounted side-by-side with their lens assemblies 94 and 95 in stereoscopic arrangement (with their optical axes in parallel or convergent alignment). The cameras 92 may be separated by any suitable distance to provide an appropriate stereoscopic view. The two cameras 92 may be linked mechanically to control the distance or angle between the cameras 92. Between the two lens assemblies 94 and 95, there is a bright LED light 96 to provide spot illumination onto the operative site.

Figure 13:
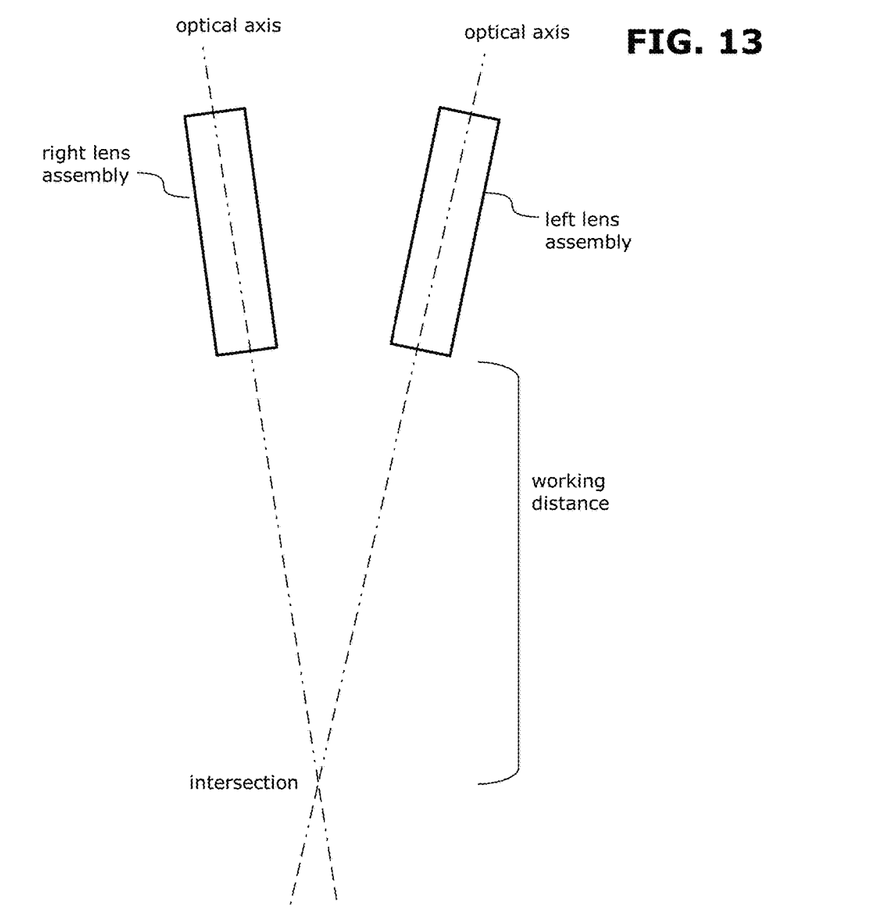
FIG. 13 shows an example of two lens assemblies being in convergent alignment.

The two optical axes of the stereoscopic camera module may be set parallel to each other or at a convergent angle. In some embodiments, the two lens assemblies of the stereoscopic camera module are set at a convergent angle. The interaxial convergence may be measured by the distance at which the optical axes meet. FIG. 13 shows an example of the two lens assemblies being in convergent alignment. There is an optical axis that passes through each lens assembly. These two axes converge at some point in space in front (intersection) of the lens assemblies. This distance from the lens assemblies to the point of intersection (or the target object) is generally known as the working distance. The angle of convergence of the two lens assemblies will vary depending on the length of this working distance, with shorter working distances translating to larger angles of convergence. In some embodiments, the two lens assemblies have an angle of convergence such that their optical axes are convergent at a working distance in the range of 2.5-150 cm; and in some cases, in the range of 0.1-1 meter (10-100 cm).

In some embodiments, the stereoscopic video camera module has optical magnification capability to provide a magnified view of the scene. Any suitable optical magnification configuration can be used, including optical telescope or optical microscope configurations. In some cases, the optical magnification power is at least 2×. Having a magnified view may be useful when performing microsurgery requiring visualization of fine anatomic structures. In some embodiments, the optical magnification power is adjustable by the user (e.g. by a controller as described above). In some embodiments, the stereoscopic video camera module further comprises an illumination source to illuminate the scene being captured (e.g. medical procedure site). The illumination source may be any conventional lighting component that produces visible light of sufficient intensity for illumination, such as LED, xenon, halogen, incandescent, etc.

My invention can be implemented in a variety of different uses, including personal, industrial, or commercial purposes. One setting where my invention can be used is in performing a medical procedure. As used herein, the term "medical procedure" includes surgical procedures and dental procedures. In some embodiments, my invention is a method of performing a medical procedure.

In the medical procedure, the clinician wears a head-worn apparatus of my invention. The head-worn apparatus is in communication with a stereoscopic camera module and receives stereoscopic video images therefrom. The stereoscopic camera module is directed to the site on the patient where the medical procedure is being performed to capture a view of the medical procedure site. The clinician performs the medical procedure while viewing the overlay image shown on the head-worn apparatus. The clinician who wears the head-worn image display apparatus is the same clinician who performs the medical procedure. While visualizing the stereoscopic overlay image of the medical procedure site, the clinician can also have a direct view of the external environment (such as the procedure site itself) around the periphery of the overlay image.

The camera module may be set at a distance from the procedure site on the patient comparable to the working distance typically experienced by clinicians when performing medical procedures (i.e. working distance). In some embodiments, the camera module is set at a distance of 2.5-150 cm from the medical procedure site; and in some cases, 15-70 cm from the medical procedure site. This may depend on user preferences, height of the user, height of the table, type of surgery being performed, location of the procedure site on the patient, space requirement for hands to work under the camera module, and whether the user is sitting or standing.

FIG. 11 shows an example of a medical procedure being performed according to my invention. The surgeon 100 is performing a surgical operation on a patient 106 who is lying on an operating table 107. As shown here, the surgeon 100 is using an example of a stereoscopic video system of my invention. A stereoscopic camera module 90 is mounted on an articulated arm 101 attached to a floor stand 103 so that the camera module 90 can be moved and pointed in various directions as needed. The stereoscopic camera module 90 is directed at the operative site on the patient 106. The mounting platform for the stereoscopic camera module 90 also has a wireless transmitter 108 for transmitting image data from the stereoscopic camera module 90 to the head-worn display apparatus 102.

The surgeon 100 is wearing the head-worn display apparatus 102, which comprises an image display assembly, which includes a light occlusion element. There is a foot controller 104 which operates to control both the camera module 90 and the head-worn display apparatus 102. Initially, the overlay image is turned-off so that the surgeon 100 can see through the display assembly to directly view the operative site on the patient 106. When the surgeon 100 is ready to view the overlay image, the surgeon presses a pedal on the foot controller 104 to turn-on the overlay image and also activate the light occlusion element to switch from transparent "see through" viewing mode to opaque "see around" viewing mode. To perform microsurgery at the operative site, the surgeon 100 then presses another pedal on the foot controller 104 to increase the magnification of the camera module 90.

Figure 14:
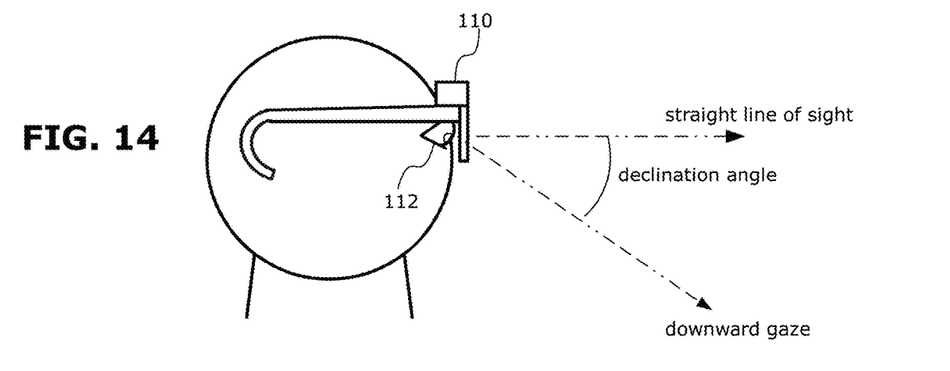
FIG. 14 shows a side-view of a user wearing a head-worn image display apparatus.

Positioning the overlay image lower in the user's visual field may be advantageous because it can resemble the configuration of some conventional surgical loupes in which the lenses are mounted at a declination angle. Providing a viewing angle that is more familiar to surgeons may promote acceptance and allow surgeons to use surgical techniques already developed using surgical loupes. FIG. 14 is provided to help explain this advantageous effect. Shown here is a side-view of a user wearing a head-worn image display apparatus 110. As compared to the user's straight-ahead line-of-sight, the overlay image is provided at a position where the user can view the image by a downward gaze. The angle between the straight-ahead line-of-sight and the direction of the downward gaze (of the user's eye 112) is the declination angle. While viewing the image lower in their visual field, the clinician may be able to shift their gaze upward to see other objects or activities relevant to the medical procedure they are performing, such as seeing where their hands are positioned, receiving surgical instruments from an assistant into their hand, seeing where the surgical instruments are positioned, seeing the layout of other surgical equipment, seeing patient monitor displays, seeing the condition of the patient, seeing and interacting with other personnel such as the surgical assistant, operating room technician, or anesthesiologist.

Figure 15A:
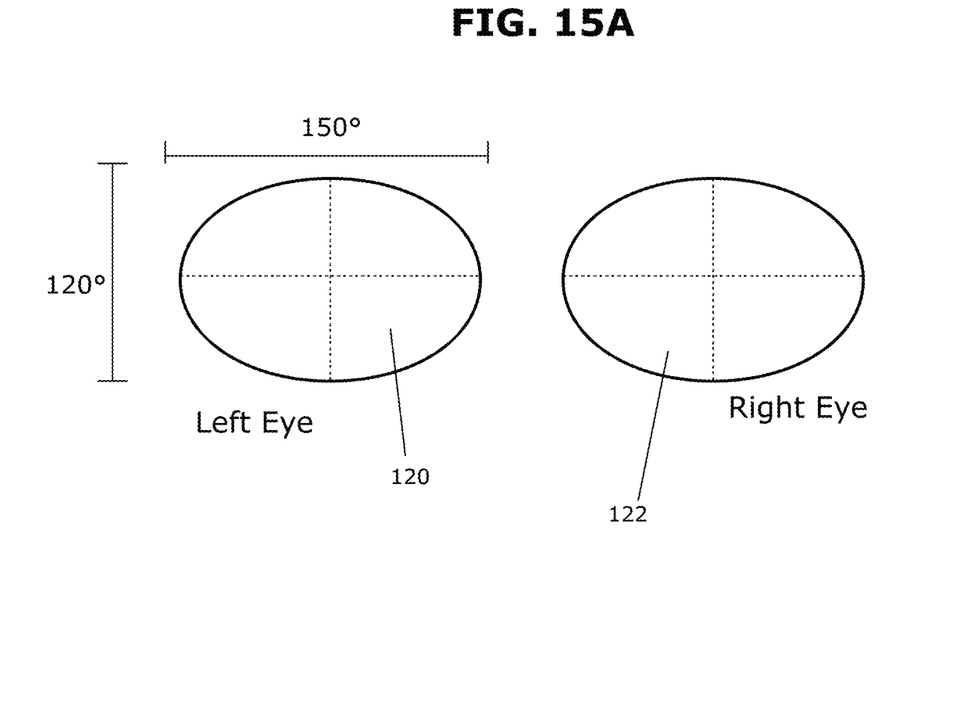
FIGS. 15A and 15B show the quadrants of the user's visual field.
Figure 15B:
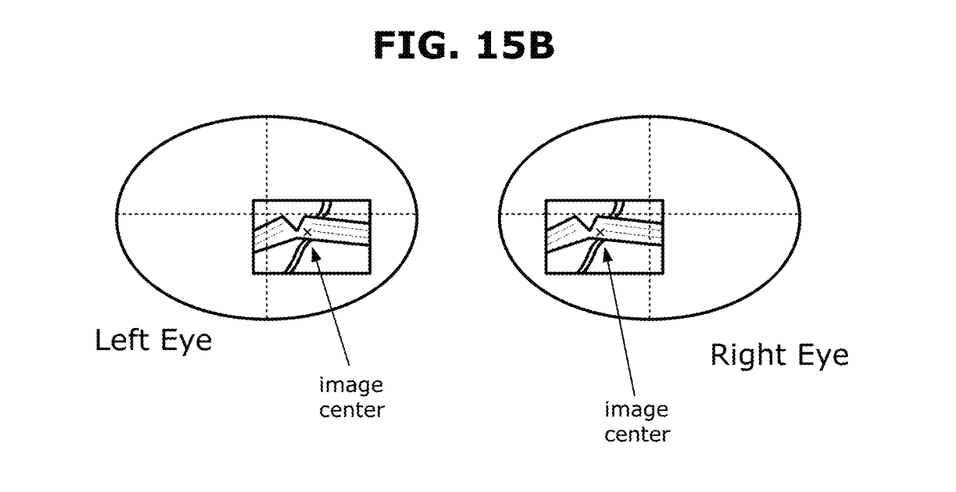

Similarly, positioning the overlay image closer to the medial side of the user's visual field (for each eye) may be advantageous because this allows the surgeon to shift their gaze laterally around the overlay image to see other objects or activities relevant to the medical procedure they are performing. FIGS. 15A and 15B are provided to explain the lower and medial portions of the user's visual field. FIG. 15A shows the visual field for the left and right eyes. Typically, the instantaneous monocular (one eye) visual field is roughly oval in shape and measures about 150° horizontally and about 120' vertically. The center of the field of vision where the two centerline axes meet is the person's straight-ahead gaze, parallel to the level of the ground, at a notional infinite distance point in the horizon. For the purposes of framing my invention, the visual field can be divided into four quadrants defined by a vertical and horizontal axis line. FIG. 15B shows the overlay image being viewed through each eye; the center of each image is indicated by the "x" mark, which is determined in a conventional way as explained above (see FIG. 3). As seen here, each overlay image is positioned in the user's visual field such that the center is in the lower medial quadrant 120 and 122 of the visual field (for that particular eye).

Because the head-worn apparatus uses a non-immersive display system, the computer-processed overlay image does not occupy the user's entire visual field. The term "non-immersive" as used herein means that the computer-processed overlay image does not occupy the user's entire visual field. Providing complete immersive viewing may not be desirable because it can impair the clinician's situational awareness. For example, when a dentist is performing a root canal, the dentist in total virtual reality immersion may not see the patient wincing in pain and raising his hand to request a pause. In another example, a surgeon in total virtual reality immersion may improperly grasp a cutting instrument that the assistant has placed into his/her hands and accidentally cut him/herself.

By having the computer-processed image occupy only a portion of the user's visual field, the user is allowed to directly view the external environment at the periphery of the overlay image being displayed. The computer-processed image may occupy only a relatively narrow part of the user's visual field. In some embodiments, the overlay image occupies less than 40° horizontally in the user's visual field; in some cases, less than 30°; in some cases, less than 25'.

Figure 16A:
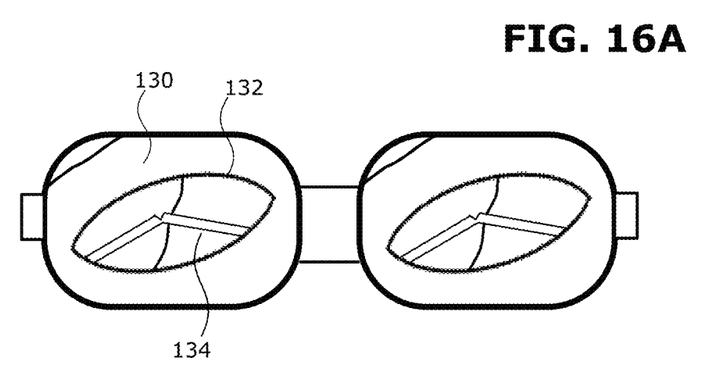
FIGS. 16A and 16B show an example of a user's view through the head-worn apparatus.
Figure 16B:
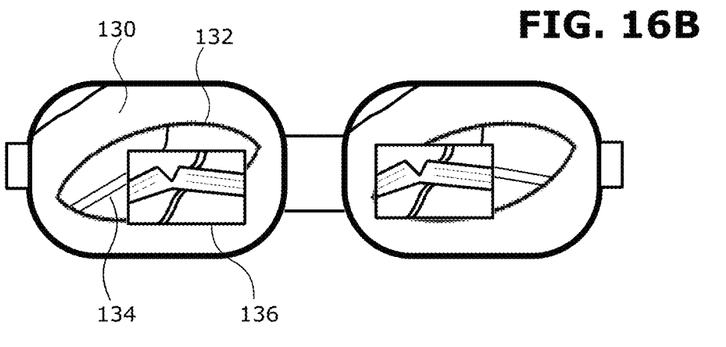

FIGS. 16A and 16B show an example of a user's view through the head-worn apparatus. As shown in FIG. 16A, the overlay image is turned-off so that the surgeon can see through the display assembly and directly view the operative procedure site on the patient's affected limb 130. With this direct view, the surgeon works on the operative site, cutting an incision 132, dissecting and retracting away tissue, and exposing the damaged nerve 134 and a blood vessel traversing it. As shown in FIG. 16B, when the surgeon is ready to work on the damaged nerve 134, the overlay image is turned-on using a foot controller, giving the surgeon a magnified stereoscopic view 136 of the damaged nerve 134. With this magnified view 136, the surgeon can work on repairing the damaged nerve 134. Meanwhile, the surgeon continues to have a direct view of the operative site at the periphery of the overlay image.

The foregoing description and examples have been set forth merely to illustrate my invention and are not intended to be limiting. Each of the disclosed aspects and embodiments of my invention may be considered individually or in combination with other aspects, embodiments, and variations of my invention. In addition, unless otherwise specified, the steps of the methods of my invention are not confined to any particular order of performance. Modifications of the disclosed embodiments incorporating the spirit and substance of my invention may occur to persons skilled in the art, and such modifications are within the scope of my invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. A stereoscopic video system for a user in performing a medical procedure, comprising:
   (a) stereoscopic video camera module with optical magnification;
   (b) a head-worn image display apparatus comprising:
      (i) a support frame; and
      (ii) a non-immersive image display assembly that is in communication with and receives video images from the stereoscopic video camera module, the display assembly comprising:
      a first display component that generates the left-side images for display;
      a second display component that generates the right-side images for display;

a left-side optical image surface or interface to provide the left-side image for viewing by the user's left eye, wherein the image surface or interface is at least partially transparent;

a right-side optical image surface or interface to provide the right-side image for viewing by the user's right eye, wherein the image surface or interface is at least partially transparent;

wherein the head-worn display apparatus is physically separate from the stereoscopic video camera module; and wherein the displayed images do not shift based on tracking of the user's head position or movement, and instead remains focused on the medical procedure site.

2. The system of claim 1, wherein the head-worn image display apparatus lacks a gyroscope or accelerometer that is configured to track the user's head position or movement.

3. The system of claim 1, wherein the stereoscopic camera module has optical magnification capability, and the images provided are magnified views of the medical procedure site; and wherein the image display assembly simultaneously provides both a magnified view of the medical procedure site as well as a direct, unmagnified view of the medical procedure site.

4. The system of claim 1, wherein each of the left-side image and the right-side image occupies less than 40° horizontally in the user's visual field.

5. The system of claim 1, wherein the stereoscopic video camera module comprises two lens assemblies set at an angle that is convergent at a working distance in the range of 10-100 cm.

6. The system of claim 1, wherein the first display component comprises a left display panel, and the left-side image surface or interface is the left display panel;

wherein the second display component comprises a right display panel, and the right-side image surface or interface is the right display panel;

wherein the distance between the center of the left display panel and the center of the right display panel is 10 cm or less.

7. The system of claim 6, wherein the distance between the center of the left display panel and the center of the right display panel is 8 cm or less.

8. The system of claim 6, wherein the center of the left-side image and the center of the right-side image are each located in a medial lower quadrant of each of the user eye's visual field.

9. The system of claim 1, wherein the image display assembly comprises an optical relay system in which the left-side image surface or interface is a left-side projection surface for the first display component; and in which the right-side image surface or interface is a right-side projection surface for the second display component;

wherein the distance between the center of the left-side projection surface and the center of the right-side projection surface is 10 cm or less.

10. The system of claim 9, wherein the distance between the center of the left-side projection surface and the center of the right-side projection surface is 8 cm or less.

11. The system of claim 9, wherein the center of the left-side image and the center of the right-side image are each located in a medial lower quadrant of each of the user eye's visual field.

12. The system of claim 1, further comprising one or more light occlusion elements that can change the amount of light transmitted through each image surface or interface.

13. The system of claim 12, wherein the head-worn image display apparatus can be selected between two or more stages that comprise:

(i) displaying the left-side and right-side images with the light occlusion element(s) in opaque mode; and (ii) deactivating display of the left-side and right-side images with the light occlusion element(s) in transparent mode.

14. The system of claim 12, further comprising a foot-operated controller that controls the light occlusion element(s).

15. The system of claim 1, further comprising a controller that controls one or more operations of the head-worn image display apparatus.

16. The system of claim 15, wherein the controller is configured to switch the left-side and right-side images on/off.

17. The system of claim 15, wherein the controller controls the head-worn image display apparatus to select between two or more stages that comprise:

(i) displaying the left-side and right-side images with the light occlusion element(s) in opaque mode such that the images occlude the view of the external scene; and (ii) deactivating display of the left-side and right-side images with the light occlusion element(s) in transparent mode.

18. The system of claim 15, wherein the controller is a foot-operated controller.

19. The system of claim 16, wherein the controller is a foot-operated controller.

20. The system of claim 17, wherein the controller is a foot-operated controller.

* * * * *